United States Patent [19]
Knollenberg

[11] 3,956,616
[45] May 11, 1976

[54] METHOD AND APPARATUS FOR GENERATING A STATISTICAL BASIS

[76] Inventor: Robert G. Knollenberg, 632 Peakview, Boulder Heights, Colo. 80302

[22] Filed: May 6, 1974

[21] Appl. No.: 466,932

[52] U.S. Cl. .................. 235/92 CC; 235/92 CA; 235/92 CP; 235/92 PL; 235/92 R
[51] Int. Cl.² ........................................ H03K 21/06
[58] Field of Search......... 235/92 PC:92 CA, 92 CV, 235/92 CC, 92 CP, 92 PL, 92 MS, 92 PE

[56] References Cited
UNITED STATES PATENTS

| | | |
|---|---|---|
| 3,391,275 | 7/1968 | Bullock et al. ................. 235/92 CA |
| 3,673,391 | 6/1972 | Lougheed ...................... 235/92 EV |
| 3,737,633 | 6/1973 | Collineau ...................... 235/92 R |
| 3,740,532 | 6/1973 | Esch ............................ 235/92 EV |
| 3,813,525 | 5/1974 | Kitterman et al. ............. 235/92 CA |

*Primary Examiner*—Mark E. Nusbaum
*Assistant Examiner*—John P. Vandenburg
*Attorney, Agent, or Firm*—Thomas W. O'Rourke

[57] ABSTRACT

Method and apparatus for selecting data wherein the acceptability of the data is a function of a measurable quality, such as duration, of a specific event relative to the current average, or other statistical threshold, of such quality of a number of events. The magnitude of event characteristic is measured and provided as a signal. Deviations from the threshold are provided to an up-down counter in which the threshold is stored and, accordingly, updated. If the event magnitude, as registered in an up-counter, exceeds the updated threshold stored in the up-down counter, a digital comparator indicates this and up counts the up-down counter to the extent the event exceeds the threshold. If the event magnitude is less than the stored threshold, the up-down counter is down-counted an amount corresponding to the difference between the event magnitude and the stored threshold. A currently updated threshold is thus maintained in the up-down counter. Weighting can be provided by, for instance, varying the clock frequency of the up-count, and the clock frequency of the down-count, to the up-down counter.

13 Claims, 4 Drawing Figures

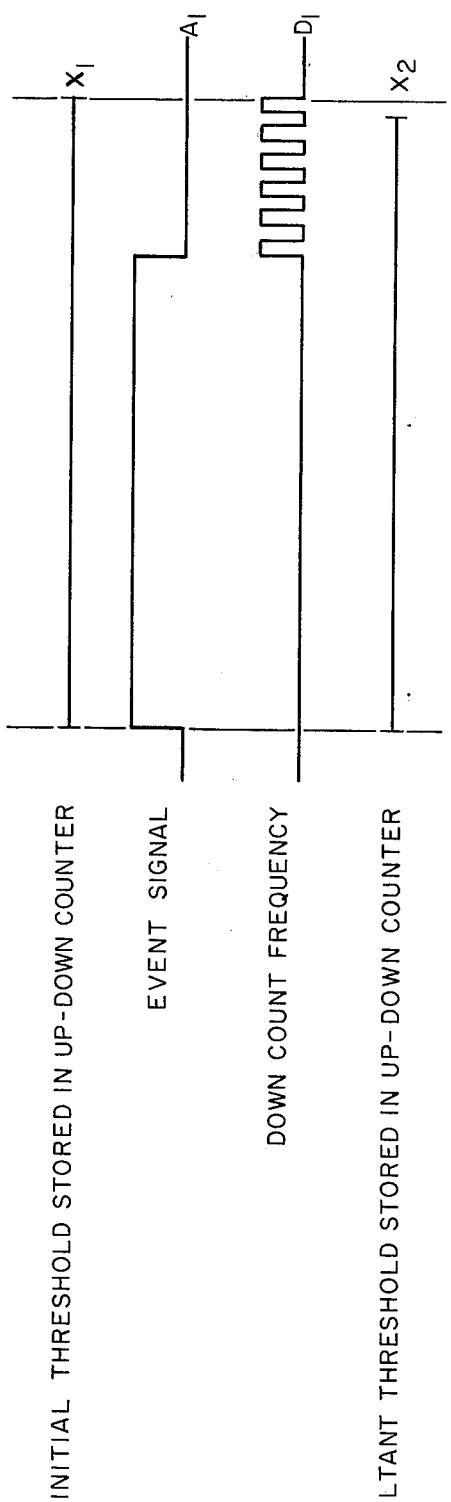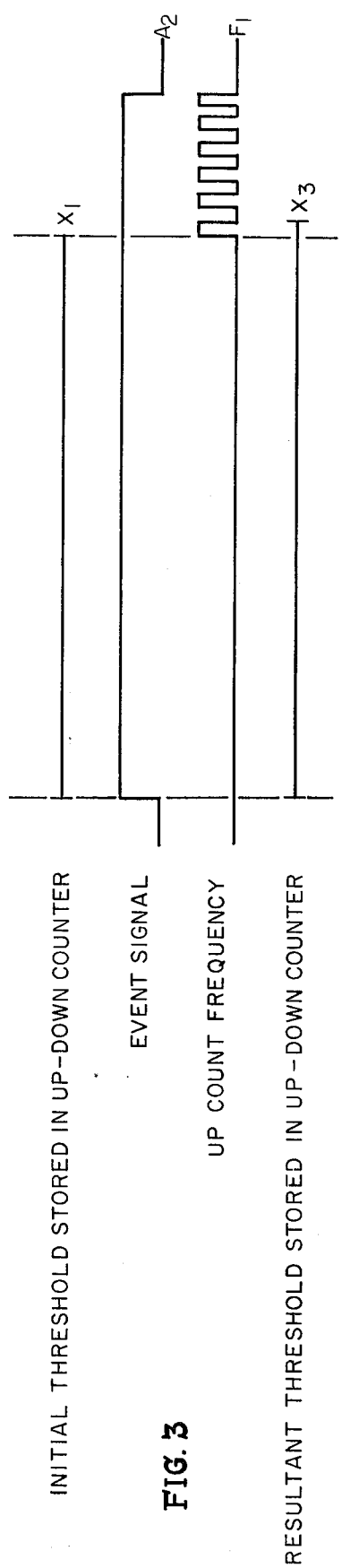

3,956,616

METHOD AND APPARATUS FOR GENERATING A STATISTICAL BASIS

BACKGROUND OF THE INVENTION

1. Field of the Invention

The present invention relates generally to a method and apparatus for discriminating between datum as a function of an input from a specific even contributing the datum relative to a weighted average, or other threshold, of the data from a number of similar events. More specifically, the invention relates to a method and apparatus for continually updating the average, or other similar threshold, of a number of events, and selecting only those events which related to the threshold in a desired manner, i.e., deviated from the threshold a predetermined positive or negative amount.

2. Description of the Prior Art

The necessity of accepting or rejecting specific datum based upon the nature of a specific corresponding event providing such datum exists for a number of measurements. An example of such a requirement is the measurement of particles by means of scattered radiation as the particle passes through a beam of radiation. Since the beam edges are usually of less intensity than the center portions of such a beam, the data for particles passing through the edges of the beam are spurious in recording the particle as being of a smaller size as a result of less scattered radiation. However, since the particles will be moving at a substantially constant average velocity, particles passing through the edges of the beam induce scattering and a resulting signal for a shorter period than do particles passing through the beam proper. Accordingly, the validity of the datum is a fraction of the duration of the specific event. Thus, only datum exceeding a predetermined threshold would be considered valid. A similar requirement may exist for many other data-gathering operations. The problems and requirements will be considered with regard to duration with the understanding that parallel discussions exist for other parameters.

One rather common approach to the problem is to provide a fixed threshold duration below which the events are discounted. However, with a fixed threshold, experimental variations other than relative duration, i.e., a variation in the average particle velocity, will undesirably vary the percent of events which are accepted or rejected.

Mechanical means can also be utilized to preclude unacceptable data. For instance, with respect to the particle measurement apparatus, masks or conduits can be employed to guide the particles only through the center of the beam. The disadvantage of this approach lies in the fact that such masks or conduits themselves influence the flow of particles, particularly when the particles are of substantial size relative to the beam, and, thus, introduce an uncertainty into the results.

SUMMARY OF THE INVENTION

The present invention, which provides a heretofore unavailable improvement over previous data selection methods and apparatus, comprises an approach in which a running mean, average, weighted average or other selected statistical basis is established. Individual events are compared to the running average, and accepted only if properly related to such threshold value. The extent to which the event exceeds the threshold is added to the threshold, or, alternatively, the extent to which the event falls short of the threshold is subtracted from the threshold value. These updatings can be accomplished in a weighted manner as to number of events, or as to the significance of the sense of the deviation, if desired. In this manner, changes in experimental conditions, i.e., a change in the average velocity of particles passing through a beam, are constantly updated and the relative percent of accepted/rejected data can be maintained essentially constant.

With specific reference to the particle measurement environment, particles passing through a beam of radiation are measured by means of substantial scattered radiation detected by photodiodes and converted to a logic level signal. The intensity of scattered radiation detected determines the size of the particle. Accordingly, particles passing through the edge of a beam, whereat the beam intensity is less than that of the center portion of the beam, will be recorded as undersized. For that reason, it is desirable that data for particles passing through the beam in less than a threshold period of time be rejected. Events are accepted as valid data if the threshold is equaled or exceeded. The variation between accepted and rejected events and the threshold are included in the threshold.

As a more specific illustration, a signal from a photodiode may be used to gate an oscillator to provide a digital input signal which is maintained for the duration of the event, or until the threshold value in an up-down counter is reached, whichever occurs later. An up-counter records the digital input signal. Comparison between the duration of the digital input signal and a threshold duration stored in an up-down counter is made by a digital comparator. If the input from the sensor ceases before the count stored in the up-down counter is reached, a down-count frequency is initiated and applied to the down-count input of the up-down counter.

Alternatively, if the signal from the photodiode persists until the digital input signal exceeds the count stored in the up-down counter, an up-count frequency is initiated upon recognition by a digital comparator of an equivalency between the count in the up-counter, as a result of the digital input signal, and the count stored in the up-down counter. The up-count frequency is then applied to the up-count input of the up-down counter and maintained until the signal from the sensor ceases. Generally, with regard to the specific illustration, initiation of the up-count frequency also indicates that the sensor signal represents valid datum. However, the start of the down-count frequency could similarly indicate valid datum in other circumstances.

In some instances, it may be desirable to accummulate a significant number of events before changing the count in the up-down counter. This is accomplished by providing decades of up-down count which must be exceeded before a signal is applied to the up-down counter in communication with the digital comparator. Further, by generating the up-count frequency and down-count frequency from oscillators of differing frequencies, inputs of identical absolute magnitude can be weighted with regard to the count in the up-down counter. Thus, by varying the frequencies of the oscillators providing the inputs, variations in the acceptance threshold can be established.

Accordingly, an object of the present invention is to provide a new and improved method and apparatus for accepting or rejecting datum depending upon the nature of the datum relative to an updated statistical sampling of similar data.

Another object of the present invention is to provide a new and improved method and apparatus for accepting or rejecting datum depending on a measured condition thereof relative to a statistical threshold for a number of events in which the threshold for acceptance or rejection can be readily established and varied.

Yet another object of the present invention is to provide a new and improved method and apparatus for selecting or rejecting datum depending on a measured or sensed condition of the datum in which the sample group influencing the threshold for acceptance or rejection can be selectively weighted as to number.

Still another object of the present invention is to provide a new and improved method and apparatus for accepting or rejecting datum depending upon the duration of the datum relative to statistical sampling of similar data duration.

These and other objects and features of the present invention will be apparent from the following description.

BRIEF DESCRIPTION OF THE DRAWINGS

In the drawings:

FIG. 2 is a diagram of signal duration in the situation in which the event duration is below the threshold;

FIG. 3 is a diagram of signal duration in the situation in which the event duration exceeds the threshold.

DETAILED DESCRIPTION OF THE INVENTION

Figure 1:
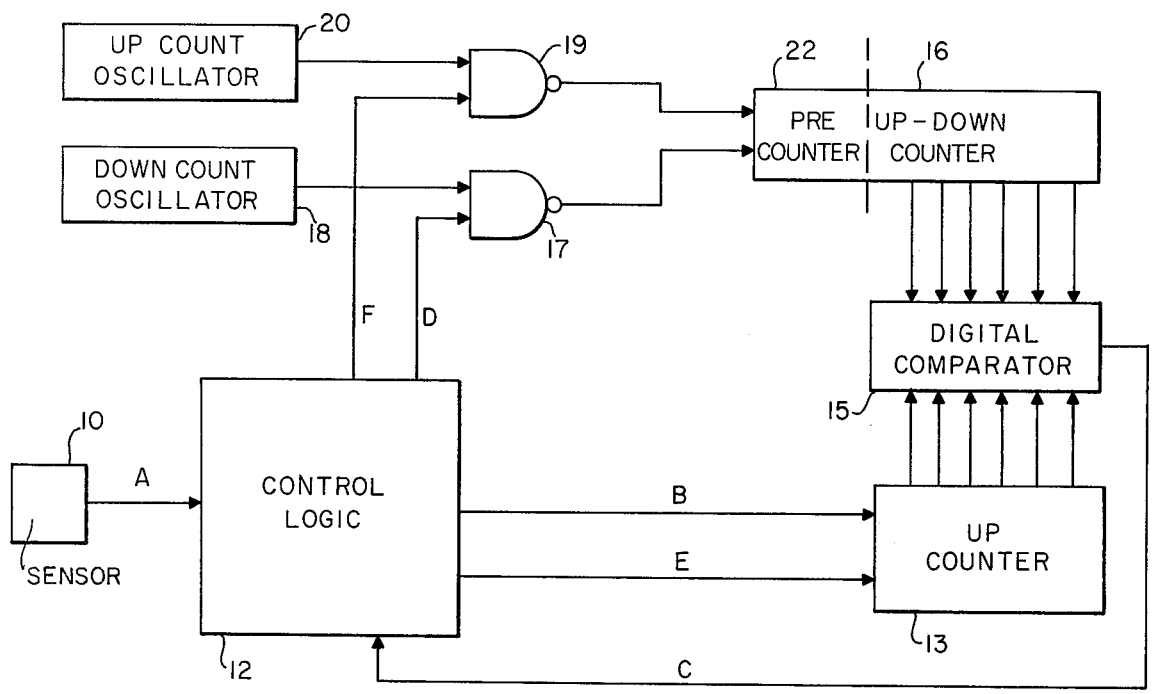
FIG. 1 is a diagrammatic illustration of the elements which constitute a data selection circuitry of the present invention.

Turning now to the drawings, wherein the invention is illustrated with particularity for purposes of clarity, a typical circuit according to the instant invention is shown in FIG. 1. Sensor 10 is activated upon the occurrence of an event and provides a logic signal A of a duration proportional to the magnitude of the characteristic being measured to logic control 12. Logic control 12, upon receipt of signal A, activates an internal gated oscillator which provides digital input signal B to the input of up-counter 13. Digital input signal B is maintained until termination of signal A from sensor 10, or until a threshold condition as described below is reached, whichever is later.

Digital comparator 15 compares the count in up-counter 13 from digital input signal B with a count as a result of inputs from previous events recorded in up-down counter 16. If the count in up-counter 13 reaches the count in up-down counter 16, digital comparator 15 either provides or terminates, according to the specific logic, signal C to logic control 12.

Assuming the case in which signal C is initiated upon equivalency of the count in up-counter 13 and up-down counter 16, the gated oscillator providing digital input signal B is latched in an operative mode until signal C from digital comparator 15 is received at logic control 12. However, if the signal A from sensor 10 terminates prior to the time of equivalency of count between up-counter 13 and up-down counter 16, logic control 12 initiates signal D to gate 17 thereby providing the frequency from down-count oscillator 18 to the down-count input of up-down counter 16. If datum below the threshold is desired, signal D also indicates datum acceptance. This down-count condition exists until equivalency is reached between the count in up-counter 13 and up-down counter 16, whereupon digital comparator 15 provides signal C to logic control 12 thereby terminating both input digital signal B and signal D to gate 17 controlling down-counter oscillator 18. Up-counter 13 is concurrently reset to zero by signal E.

Alternatively, if sensor 10 is providing signal A to logic control 12 at the time digital comparator 15 indicates equivalency of count between up-counter 13 and up-down counter 16, thereby providing signal C to logic control 12, the coincidence of signal A and signal C to logic control 12 initiates signal F to gate 19. Gate 19 controls the frequency from up-count oscillator 20 to the up-count input of up-down counter 16 for the period during which signal F persists. Signal F indicates that the magnitude of the datum from sensor 10 exceeds the threshold. Up-count gate 19 is activated for so long as coincidence between signal A and signal C exists at logic control 12. However, upon termination of signal A from sensor 10, the activation of up-count gate 19 concurrently ceases. Signal E then resets up-counter 13 to zero.

From the above discussion, it will be apparent that the count to up-down counter 16 is a function of the, for instance, positive or negative difference between the magnitude of event signal A from sensor 10, and the count in up-down counter 16 at any given time corresponding to a given event. Accordingly, the count in up-down counter 16 is corrected in the appropriate sense to correspond to the duration of events actually activating sensor 10.

It is often desirable to weight the up-count input relative to the down-count input. This can be readily accomplished by varying the frequencies of down-count oscillator 18 and/or up-count oscillator 20. Such variations will weight the significance of signal D or signal F depended upon the desired threshold. Of course, down-count oscillator 18 and up-count oscillator 20 can be dispensed with if such weighting is not required and the oscillator of logic control 12 can be utilized to provide equally-weighted signals to up-down counter 16.

A pre-counter section 22 of up-down counter 16 may be utilized to dampen the effect of individual variations between a given event and the count stored in up-down counter 16. Only when the up-count or down-count exceeds that storable in pre-counter section 22 is the information provided to the stages of up-down counter 16 in communication with digital comparator 15. Several stages of precount can, of course, be employed depending upon the sample group deemed necessary to provide significant information.

The operation of the circuitry illustrated in FIG. 1 and described above will be more readily understood with reference to FIGS. 2 and 3. The initial threshold which, of course, is the count in up-down counter 16, is illustrated at $X_1$. The event signal illustrated as $A_1$ is initiated on the occurrence of an event and is shown as terminating prior to the time equivalent between the count in up-counter 13 and up-down counter 16. Accordingly, upon termination of an event signal $A_1$, down-count frequency $D_1$ is initiated and maintained until equivalency of count between up-counter 13 and up-down counter 16 is reached and recognized by digital comparator 15. When equivalence is reached, down-count frequency $D_1$ terminates, up-counter 13 is reset, and the circuitry becomes passive. However, as a result of the input of down-count frequency $D_1$ into up-down counter 16, the resultant threshold $X_2$ is diminished relative to initial threshold $X_1$.

Alternatively, as shown in FIG. 3, when the event signal $A_2$ exceeds the initial threshold $X_1$ in up-down counter 16, there is coincidence of event signal $A_2$ and output signal C from digital comparator 15 with the result of initiation of up-count oscillator frequency $F_1$. Up-count frequency $F_2$ is maintained until event signal $A_2$ ceases, whereupon operation of the circuit relative to the given even ceases and up-counter 13 is reset. However, as a result of the input of down-count frequency $F_1$ into up-down counter 16, the resultant threshold $X_3$ is increased relative to initial threshold $X_1$.

The specific nature of control logic 12 is, of course, dependent upon the nature of the characteristics being measured by sensor 10, and, accordingly, the nature of sensor 10 and resulting signal A to control logic 12. For instance, when the parameter or characteristic being measured is temperature, pressure or some other similar condition, it is not unusual for sensor 10 to include a means for providing an analogue signal. In such cases, sensor 10 may also convert the analogue signal to frequency and sample for a given length of time. In this instance, input signal A could be a digital signal with the number of pulses corresponding to the magnitude of the characteristic. Alternatively, the analogue signal could be integrated into a capacitor for a fixed length of time, and signal A would constitute a logic level signal wherein the time to discharge the capacitor through a fixed resistance would correspond to the magnitude of the characteristic. In yet another instance, the characteristic measured could be the duration of the event whereupon signal A would be initiated upon sensing of an event by sensor 10 and would be terminated when the event terminated. Thus, it follows that signal A would be a logic level signal existing contemporaneously with the occurrence of the event. Numerous other means of providing an appropriate signal A will be apparent to those skilled in the art.

Given the discussion above and the relationship between input signal A, control logic 12, and signal C from digital comparator 15, it is within the skill of the art to provide appropriate logic for any given condition. Analogue signals can be converted to digital signals. Digital comparator 15 can provide or terminate an output upon equivalency between up-counter 13 and up-down counter 16. The combinations and permutations are extensive. But, given the concept of updating up-down counter 16 depending upon the deviance of a specific event from the count in up-down counter 16, and providing a response from digital comparator 15 upon equivalency, various embodiments of control logic 12 can be readily provided by those skilled in the art.

Figure 4:
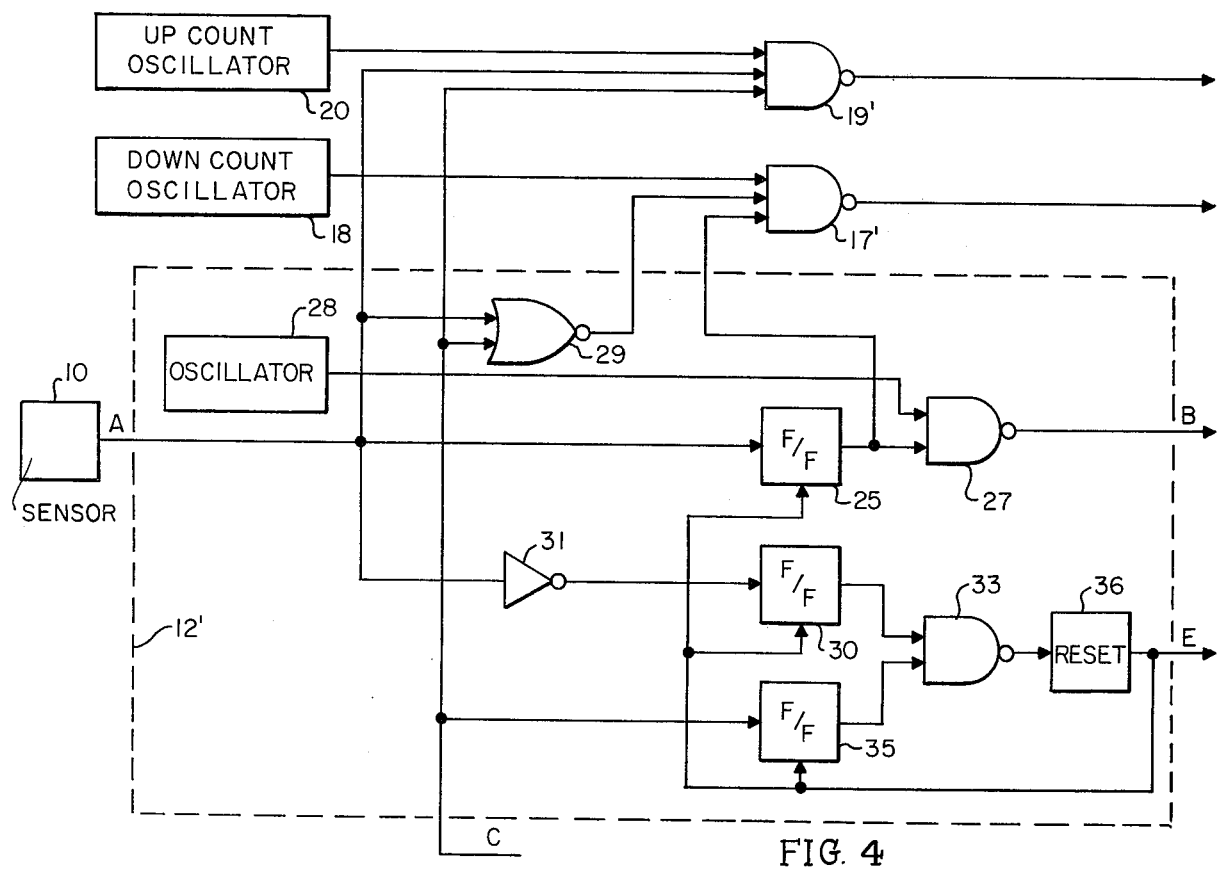
FIG. 4 is a circuit diagram of one logic circuit useful in the present invention.

By way of illustration, a specific embodiment of control logic is set forth in FIG. 4, when considered in conjunction with FIG. 1. Control logic 12' of FIG. 4 is not identical to control logic 12 shown in FIG. 1, but the interfaces of the outputs from gates 17 and 19 of FIG. 1 and 17' and 19' of FIG. 4, as well as the other similarly marked interfaces, are the same. With primary reference to FIG. 4, sensor 10 measures duration of an event and signal A is a logic level signal corresponding to the duration of the event. The leading edge of signal A triggers flip-flop 25 thereby providing an output to gate 27. Control logic oscillator 28 is controlled by gate 27, and, upon the triggering of flip-flop 25, provides output signal B. Signal A is also applied to NOR gate 29 thereby inhibiting output of a signal to gate 17'.

Upon termination of signal A prior to initiation of signal C, flip-flop 30 is activated by the trailing edge of signal A as a result of signal A passing through inverter 31. This provides one input to gate 33. However, termination of signal A also terminates the joint denial at NOR gate 29 thereby providing an output to gate 17'. The output from flip-flop 25 is also present at gate 17' thereby permitting down-count oscillator 18 to provide a down-count frequency through gate 17'. However, upon the response from digital comparator 15 upon equivalency between up-counter 13 and up-down counter 16, as shown in FIG. 1, signal C is initiated thereby activating flip-flop 35 and inhibiting NOR gate 29 and, accordingly, terminating the output from gate 17'. The output from flip-flop 35 in conjunction with the output from flip-flop 30 provides a signal from gate 33 to one-shot reset 36. Reset 36, in turn, provides signal E to reset up-counter 13, as shown in FIG. 1, to zero and also resets flip-flops 25, 30 and 35.

If, on the other hand, signal A persists until signal C occurs upon response from digital comparator 15, up-count oscillator 20 is gated through gate 19' by coincidence of signal C and signal A at gate 19'. Accordingly, up-count frequency is provided to the up-count input of up-down counter 16 in the manner illustrated in FIG. 1. Upon the initiation of signal C, flip-flop 35 is triggered providing an output therefrom to gate 33. However, as explained above, until signal A terminates, no output is provided by flip-flop 30. Upon termination of signal A, flip-flop 30, as explained above, provides an output to gate 33 thereby activating one-shot reset 36 with the results previously set forth.

Although, in view of the wide usage to which the present invention can be put, only limited embodiments have be described for purposes of illustration, it is anticipated that various changes and modifications will be readily apparent to those skilled in the art, and that such changes and modifications may be made without departing from the scope of the invention as defined by the following claims.

What is claimed is:

1. A system for generating a currently updated statistical datum threshold, comprising: an up-down counter, an up-counter, a digital comparator connected to both the up-down counter and the up-counter and responsive to an equivalency of count in the up-counter and the up-down counter, means for generating a digital input signal at least proportional to a signal measuring the magnitude of a parameter of an event, the digital input signal being applied to the up-counter, latch means to maintain the digital input signal at least until response by the digital comparator indicating equivalency of count between the up-counter and the up-down counter, down-count means providing a signal initiated by completion of the signal measuring the event parameter magnitude prior to response by the digital comparator and terminated by response by the digital comparator, the down-count means signal being ultimately applied to the down-count input of the up-down counter as a down-count frequency, up-count means providing a signal initiated by response from the digital comparator prior to completion of the signal measuring the event parameter magnitude and terminated by completion of the signal measuring the event parameter magnitude, the up-count means signal being ultimately applied to the up-count input of the up-down counter as an up-count frequency, and means to reset the up-counter upon both termination of the signal measuring the magnitude of a parameter and response from the digital comparator, whereby the magnitude of the signal measuring the event parameter is compared to a statistical signal magnitude threshold of previous signals stored as the count in the up-down counter, the count of the up-down counter is appropriately updated corresponding to the magnitude of the specific event signal relative to the statistical threshold stored in the up-down counter, and the up-count means and down-count means can be utilized to accept or reject datum of a specific event as a function of the specific event datum relative to the statistical threshold.

2. A system as set forth in claim 1 wherein the means for generating the digital input signal comprises a photosensor which generates a logic level signal measuring the magnitude of a parameter of an event, the photosensor being connected to an AND gate in conjunction with an oscillator also connected to the AND gate, whereby the digital signal output from the AND gate is a function of the duration of an event which provides light to the photosensor while the event is occurring.

3. A system as set forth in claim 2 wherein the event measured is a size of a particle passing through a light beam and includes a means for accepting data from a specific even upon coexistance of the signal from the photosensor and response from the digital comparator, whereby data of a duration shorter than the statistical threshold, which data is known to be spurious as a result of the particle passing through the edge of the light beam, are rejected.

4. A system as set forth in claim 1 wherein the up-count frequency and down-count frequency are each generated by distinct oscillators which operate at differing frequencies.

5. A system as set forth in claim 1 wherein the up-count frequency and the down-count frequency are generated by a common oscillator which also generates the digital input signal.

6. A system as set forth in claim 1 wherein the up-down counter includes at least one bit of precount.

7. A system for measuring events and characterizing datum as a function of a specific event duration relative to an updated statistical threshold of previous event duration, comprising: an up-down counter, an up-counter, a digital comparator connected to both the up-counter and the up-down counter, photosensor means for generating a logic level signal in response to and throughout the occurrence of an event, a first flip-flop responsive to the leading edge of the logic level signal from the photosensor means, oscillator means, a first AND gate receiving the output from the first flip-flop and concurrently receiving a frequency from the oscillator means to produce a digital output signal for such time as the first flip-flop is activated, the digital signal output from the first AND gate being in communication with the input of the up-counter, the logic level from the photosensor means also being applied to a NOR gate input, the output from the digital comparator providing a second NOR gate input, and the output of the NOR gate being applied to a second AND gate input in conjunction with a signal from the oscillator means and the output from the first flip-flop with the output frequency from the second AND gate being connected to the down-count input of the up-down counter, a third AND gate, the logic level signal from the photosensor means also being gated through the third AND gate in conjunction with the response signal from the digital comparator and a frequency from the oscillator means with the output from the third AND gate being connected to the up-count input of the up-down counter, the logic level signal from the photosensor means further being connected through an inverter to a second flip-flop which is thereby responsive to the trailing edge of the logic level signal, and a third flip-flop activatable by the response from the digital comparator, the output from the second flip-flop, and the third flip-flop being gated through a fourth AND gate to a one-shop reset, whereby a photosensor logic level signal initially activates and latches by means of the first flip-flop the digital output signal which is provided to the up-counter and thus to an input of the digital comparator, but, upon termination of the logic level input signal prior to response from the digital comparator, and a resulting lack of joint denial at the NOR gate, activates the second AND gate thereby providing a frequency to the down-count input of the up-down counter, and thus an indication of a "short" event or, alternatively, if the response from the digital comparator occurs prior to termination of logic level signal, coincidence of the logic level signal and the response from the digital comparator at the third AND gate provides an up-count frequency to the up-count input of the up-down counter, and thus an indication of a "long" event, and, finally, activation of the second flip-flop by the trailing edge of the logic level signal in conjunction with activation of the third flip-flop by the response from the digital comparator gates a signal through the fourthe AND gate to the one-shop reset thereby resetting the first, second and third flip-flops and the up-counter.

8. A system as set forth in claim 7 wherein the up-count frequency and down-count frequency are each generated by distinct oscillators which operate at differing frequencies and are included in the oscillator means.

9. A system as set forth in claim 7 wherein the up-count frequency and the down-count frequency are generated by the oscillator means which is a single oscillator which also generates the digital input signal.

10. A system as set forth in claim 7 wherein the up-down counter includes at least one bit of precount.

11. A method for generating a currently updated statistical threshold, comprising: generating a digital input signal at least proportional to a signal measuring the magnitude of a parameter of an event, latching the digital input signal, up-counting an up-counter in response to the digital signal, continually comparing the count in the up-counter to an existing count in an up-down storing processed counts from previous events, generating a response upon equivalency of the count in the up-counter and the count in the up-down counter, generating a down-count frequency and down-counting the up-down counter upon termination of the signal measuring the event parameter magnitude prior to the equivalency response, and continuing the down-count frequency until the equivalency response is generated, generating an up-count frequency and applying the frequency to the up-count input of the up-down counter upon generation of the equivalency response prior to termination of the signal measuring the event parameter magnitude, and, upon both termination of the signal measuring the event parameter magnitude and generation of the equivalency response, terminating the digital input signal and resetting the up-counter to zero, whereby the currently updated statistical threshold of the magnitude of previous event parameters is stored in the up-down counter and the magnitude of a parameter of a current event can be compared to and characterized as being greater than or less than the threshold, and the threshold is updated appropriately to reflect the current event.

12. A method as set forth in claim 11 wherein datum from an event is accepted upon generation of the down-count frequency.

13. A method as set forth in claim 11 wherein datum from an event is accepted upon generation of the up-count frequency.

* * * * *

UNITED STATES PATENT AND TRADEMARK OFFICE
CERTIFICATE OF CORRECTION

PATENT NO. : 3,956,616
DATED : May 11, 1976
INVENTOR(S) : Robert G. Knollenberg

It is certified that error appears in the above—identified patent and that said Letters Patent are hereby corrected as shown below:

Column 1, line 9, delete "even" and substitute --event--.

Column 1, line 35, delete "fraction" and substitute --function--.

Column 5, line 10, delete "even" and substitute --event--.

Column 5, line 27, after "integrated" insert --directly--.

Column 7, line 27, delete "even" and substitute --event--.

Column 8, line 53, after "down" insert --counter--.

Signed and Sealed this

Third Day of August 1976

[SEAL]

Attest:

RUTH C. MASON
*Attesting Officer*

C. MARSHALL DANN
*Commissioner of Patents and Trademarks*